United States Patent
Schulze zur Wiesche et al.

(10) Patent No.: US 8,900,329 B2
(45) Date of Patent: *Dec. 2, 2014

(54) PRETREATMENT AGENTS FOR KERATIN FIBERS COMPRISING 4-MORPHOLINO-METHYL-SUBSTITUTED SILICONE(S)

(71) Applicant: Henkel AG & Co. KGaA, Duesseldorf (DE)

(72) Inventors: Erik Schulze zur Wiesche, Hamburg (DE); Monika Nebel, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/279,628

(22) Filed: May 16, 2014

(65) Prior Publication Data

US 2014/0245542 A1    Sep. 4, 2014

Related U.S. Application Data

(63) Continuation of application No. PCT/EP2012/070919, filed on Oct. 23, 2012.

(30) Foreign Application Priority Data

Nov. 29, 2011 (DE) .......................... 10 2011 087 344

(51) Int. Cl.
*A61Q 5/10* (2006.01)
*A61Q 5/00* (2006.01)
*A61K 8/898* (2006.01)

(52) U.S. Cl.
CPC . *A61K 8/898* (2013.01); *A61Q 5/10* (2013.01); *A61Q 5/004* (2013.01)
USPC ........................ 8/405; 8/406; 8/581; 424/70.1

(58) Field of Classification Search
CPC .......... A61Q 5/10; A61K 8/585; A61K 8/898
USPC ............................... 8/405, 406, 581; 424/70.1
See application file for complete search history.

(56) References Cited

U.S. PATENT DOCUMENTS 6,824,764 B2 * 11/2004 Devin-Baudoin et al. ... 424/70.1

OTHER PUBLICATIONS

STIC Search Report dated Jun. 17, 2014.*

* cited by examiner

*Primary Examiner* — Eisa Elhilo
(74) *Attorney, Agent, or Firm* — David K. Benson

(57) ABSTRACT

The invention relates to pretreatment agents for keratin fibers, which include, based on its weight, 0.00001 to 10 wt. % of at least one 4-morpholino-methyl-substituted silicone, which includes in each case at least one of the structural units of the formulae (I), (II) and (III) described herein, wherein * represents a bond to one of the structural units (I), (II) or (III) or an end group B (Si-bound) or D (O-bound); B represents a group —OH, —O—Si(CH$_3$)$_3$, —O—Si(CH$_3$)$_2$OH, —O—Si(CH$_3$)$_2$OCH$_3$; D represents a group —H; —Si(CH$_3$)$_3$, —Si(CH$_3$)$_2$OH, —Si(CH$_3$)$_2$OCH$_3$; A represents an O-bound structural unit (I), (II) or (III) or a O-bound oligomeric or polymeric radical including structural units of the formulae (I), (II) or (III) or half of a connecting O atom to a structural unit (III) or represents —OH; n, m and o represent whole numbers between 1 and 1000 and include at least 50 wt. % of water.

10 Claims, No Drawings

PRETREATMENT AGENTS FOR KERATIN FIBERS COMPRISING 4-MORPHOLINO-METHYL-SUBSTITUTED SILICONE(S)

FIELD OF THE INVENTION

The present invention generally relates to cosmetic compositions, which protect keratinic fibers against oxidative effects.

BACKGROUND OF THE INVENTION

During the dyeing and blonding of hair, the problem arises that, because of the aggressive agents, irritation of the scalp and damage to the keratinic fiber can occur. In particular, the natural hydrophobicity of the keratinic fiber is reduced, since the coloring or lightening agents must first make the hair capable of being penetrated in order to develop their action. However, on the one hand the water-repelling action is a natural protection of hair, and on the other hand parameters desired by the consumer, such as gloss, suppleness, handle and "fall" of the hair, are closely linked with it.

In order to overcome the above disadvantages, there are so-called pretreatment agents on the market which are intended to protect the hair against the aggressive effect. However, these often make the hair heavier or negatively affect the success of subsequent lightening or dyeing of hair.

The present invention was based on the object of providing agents which overcome the above disadvantages without counteracting the success of a subsequent oxidative treatment. In particular, agents were to be provided which do not make the hair heavier and which achieve the desired effect even when the pretreatment does not take place immediately before the oxidative treatment, as a result of which the period between pretreatment and dyeing or blonding can be extended.

The use of aminated silicones in hair care is prior art. These are widely used in shampoos and particularly in conditioners in order to develop care effects there. Thus, EP 1 771 144 B1 discloses hair-conditioning agents with amino functional silicones. The agents described there are after-treatment agents.

European patents EP 1 312 334 B1 (amino silicone and thickener) and EP 1 312 335 B1 (amino silicone and conditioner) also disclose hair after-treatment agents. In the former document, extremely water-rich formulations are also disclosed.

BRIEF SUMMARY OF THE INVENTION

A pretreatment agent for keratinic fibers including, based on its weight, a) 0.00001 to 20 wt. % of at least one 4-morpholinomethyl-substituted silicone, which in each case comprises at least one of the structural units of formulae (I), (II) and (III)

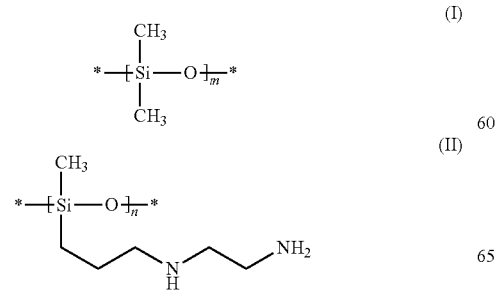

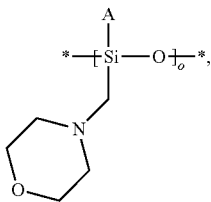

where * denotes a bond to one of the structural units (I), (II) or (III) or an end group B (Si-bound) or D (O-bound), B denotes a group —OH, —O—Si(CH$_3$)$_3$, —O—Si(CH$_3$)$_2$OH, —O—Si(CH$_3$)$_2$OCH$_3$, D denotes a group —H; —Si(CH$_3$)$_3$, —Si(CH$_3$)$_2$OH, —Si(CH$_3$)$_2$OCH$_3$, A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, n, m and o denote integers between 1 and 1000; and b) at least 50 wt. % water.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that a pretreatment of the keratinic fibers with special 4-morpholinomethyl-substituted silicones within a specific period before an oxidative treatment leads to significantly improved hair protection without the results of the oxidative treatment being negatively affected.

The present invention provides in a first embodiment pretreatment agents for keratinic fibers including, based on their weight,
a) 0.00001 to 20 wt. % of at least one 4-morpholinomethyl-substituted silicone, which in each case comprises at least one of the structural units of formulae (I), (II) and (III)

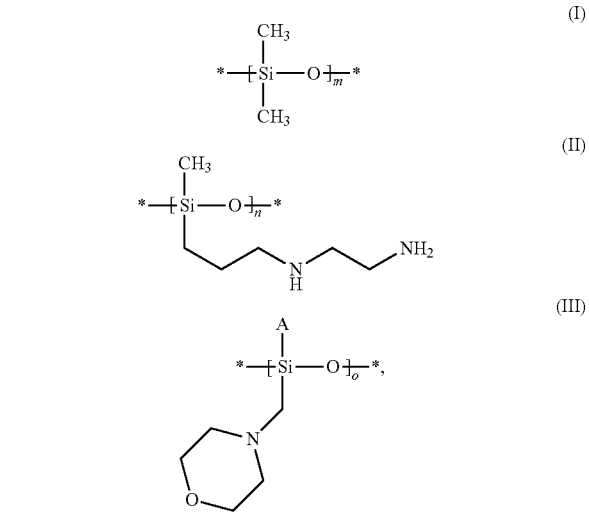

where
* denotes a bond to one of the structural units (I), (II) or (III) or an end group B (Si-bound) or D (O-bound),
B denotes a group —OH, —O—Si(CH$_3$)$_3$, —O—Si(CH$_3$)$_2$OH, —O—Si(CH$_3$)$_2$OCH$_3$,
D denotes a group —H; —Si(CH$_3$)$_3$, —Si(CH$_3$)$_2$OH, —Si(CH$_3$)$_2$OCH$_3$,
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, n, m and o denote integers between 1 and 1000 b) at least 50 wt. % water.

The pretreatment agents according to the invention are water-based and include at least 80 wt. % water. Preferred agents according to the invention include even higher quantities of water, up to 99 wt. %. Particularly preferred agents according to the invention are characterized in that they include, based on the weight of the agent, 70 to 99.9 wt. %, preferably 80 to 99.5 wt. %, particularly preferably 85 to 99.25 wt. % and in particular 90 to 98 wt % water.

As active substance, the agents according to the invention include 0.00001 to 10 wt. % of at least one 4-morpholinomethyl-substituted silicone, each of which comprises at least one of the structural units of formulae (I), (II) and (III).

The structural units of formulae (I), (II) and (III) here can be present in random distribution in the molecule, but the silicones used according to the invention can also be block copolymers of blocks of the individual structural units, wherein the blocks can again be present in random distribution.

The * on the free valencies of the structural units (I), (II) or (III) here denotes a bond to one of the structural units (I), (II) or (III) or an end group B (Si-bound) or D (O-bound).

The silicones used according to the invention can be trimethylsilyl-terminated at both ends (D=—Si(CH$_3$)$_3$, B=—O—Si(CH$_3$)$_3$), but they can also be dimethylsilylhydroxy- or dimethylsilylmethoxy-terminated at one or both ends. Particularly preferably used silicones within the framework of the present invention comprise at least one terminal dimethylsilylhydroxy group, i.e. are selected from silicones where the following meanings apply:

B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH.

These silicones lead to vast improvements in the hair properties of hair treated with the agents according to the invention, and in particular to a significant reduction in the contact angle. In the structural unit (III), the residue A can denote a structural unit (I), (II) or (III) bound by an —O— or
an oligomeric or polymeric residue including structural units of formulae (I), (II) or (III) bound by an —O— or half of a connecting O atom to a structural unit (III) or —OH.

In the first case, the structural unit (III) becomes one of the structural units (IIIa), (IIIb) or (IIIc):

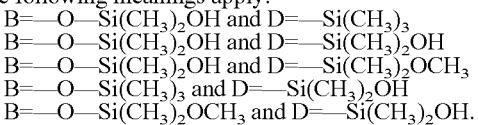
(IIIa)

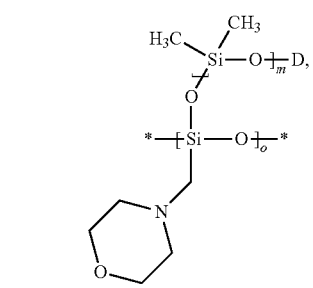
(IIIb)

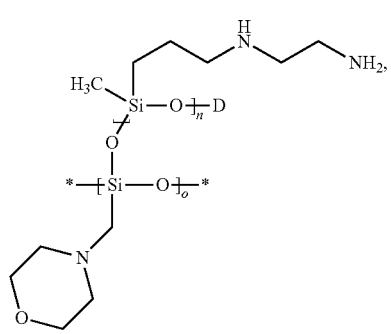
(IIIc)

with m=n=o=1 and A respectively D as defined above.

In the second case, in the above-mentioned formulae (IIIa), (IIIb) and (IIIc), the indices m, n and o can denote integers between 2 and 1000. However, the second case also covers oligomeric or polymeric residues that include at least two different structural units of formulae (I), (II) or (III), as shown in formula (IIId):

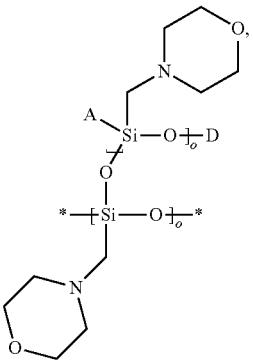
(IIId)

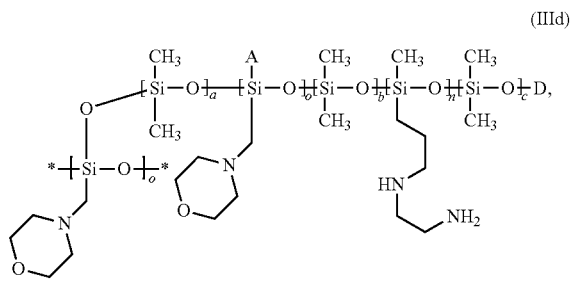

in which a, b and c denote integers between 0 and 1000, with the proviso that a+b+c>0, and also n and o denote integers between 1 and 1000.

In the third case, A denotes half of a connecting O atom to a structural unit (III) (illustrated in structural unit (IIIe)) or denotes —OH (illustrated in structural unit (IIIf))

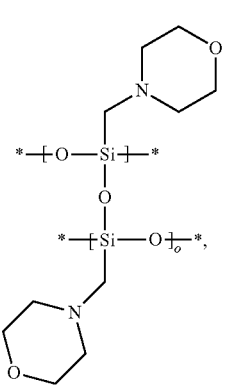
(IIIe)

-continued

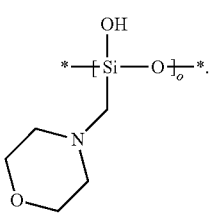
(IIIf)

As already mentioned, the structural units of formulae (I), (II) and (III) can preferably be present in random distribution. Preferred pretreatment agents according to the invention include at least one 4-morpholinomethyl-substituted silicone of formula (V)

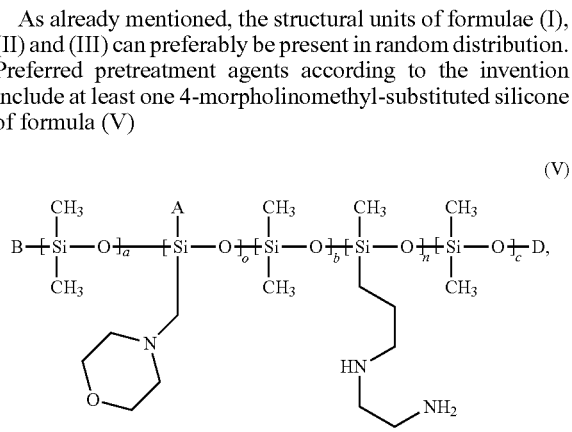
(V)

in which
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
B denotes a group —OH, —O—Si(CH$_3$)$_3$, —O—Si(CH$_3$)$_2$OH, —O—Si(CH$_3$)$_2$OCH$_3$,
D denotes a group —H; —Si(CH$_3$)$_3$, —Si(CH$_3$)$_2$OH, —Si(CH$_3$)$_2$OCH$_3$,
a, b and c denote integers between 0 and 1000, with the proviso that a+b+c>0 n and o denote integers between 1 and 1000.

Structural formula (V) is intended to clarify that the siloxane groups n and o do not necessarily have to be bound directly to an end grouping B or D. Rather, in preferred formulae (V), a>0 or b>0 applies and in particularly preferred formulae (V) a>0 and b>0, i.e. the terminal grouping B or D is preferably bound to a dimethylsiloxy grouping. In formula (V) too, the siloxane units a, b, c, n and o are preferably randomly distributed.

The silicones used according to the invention represented by formula (V) can also be trimethylsilyl-terminated at both ends (D=—Si(CH$_3$)$_3$ B=—O—Si(CH$_3$)$_3$), but they can also be dimethylsilylhydroxy- or dimethylsilylmethoxy-terminated at one or both ends. Particularly preferably used silicones within the framework of the present invention comprise at least one terminal dimethylsilylhydroxy group, i.e. are selected from silicones in which the following meanings apply:
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH.

These silicones lead to vast improvements in the hair properties of the hair treated with the agents according to the invention, and in particular to significantly improved protection during oxidative treatment.

In formula (V) too, the residue A can denote
a structural unit (I), (II) or (III) bound by an —O— or
an oligomeric or polymeric residue including structural units of formulae (I), (II) or (III) bound by an —O— or half of a connecting O atom to a structural unit (III) or —OH.

In the same way as for the statements regarding structural unit (III), formula (V) is therefore stated more precisely as one of formulae (Va), (Vb), (Vc), (Vd), (Ve) or (Vf), as disclosed in the priority document on pages 6 to 8.

The structural unit (III) respectively the siloxane units o in formulae (V) can form nido or partial cage structures via the group A if A denotes half of a connecting O atom to a structural unit (III). Pretreatment agents according to the invention which include silicones with corresponding 4-morpholinomethyl-substituted silsequioxane partial structures are preferred according to the invention, since these silicones lead to greatly improved protection of hair against oxidative treatment.

Preferred pretreatment agents according to the invention are accordingly characterized in that they include at least one 4-morpholinomethyl-substituted silicone, which comprises structural units of formula (VI)

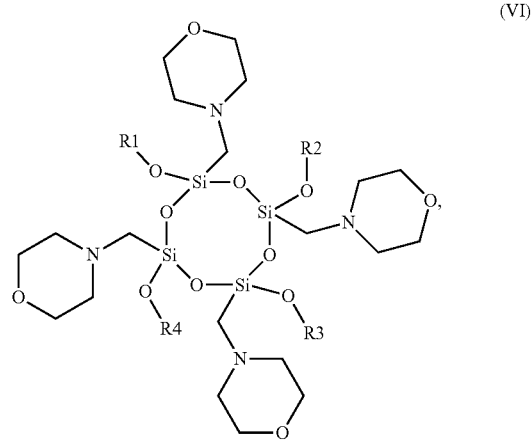
(VI)

in which
R1, R2, R3 and R4 independently of one another denote —H, —CH$_3$, a group D, a structural unit (I), (II) or (III) or an oligomeric or polymeric residue including structural units of formulae (I), (II) or (III) or two of the residues R1, R2, R3 and R4 denote a structural unit —Si(R6)(R5)- with
R5=—CH$_3$ or a structural unit of formula (I) or (II) or (III) or an oligomeric or polymeric residue including structural units of formulae (I), (II) or (III)
R6=—OH, —CH$_3$ or a structural unit of formula (I) or (II) or (III) or an oligomeric or polymeric residue including structural units of formulae (I), (II) or (III).

In preferred silicones of formula (VI) at least one of the residues R1, R2, R3 or R4 denotes an oligomeric or polymeric residue including structural units of formulae (I), (II) or (III).

In further preferred silicones of formula (VI), at least one of the residues R1, R2, R3 or R4 denotes an oligomeric or polymeric residue including structural units of formulae (I) and (II). In still further preferred silicones of formula (VI) at least one of the residues R1, R2, R3 or R4 denotes an oligomeric or polymeric residue including structural units of formulae (I) and (II) and (III).

Preferably at least one of the residues R1, R2, R3 or R4 denotes a —[—Si(CH$_3$)$_2$—O]m— grouping, i.e. an oligomer or polymer of the structural unit (I). In addition, the structural unit (II) or an oligomer or polymer thereof is preferably never bound in the molecule alone but always in random distribution with other structural units of formula (I) as one of the residues R1, R2, R3 or R4.

Preferred silicones of formula (VI) can be described by the formula (VI a)

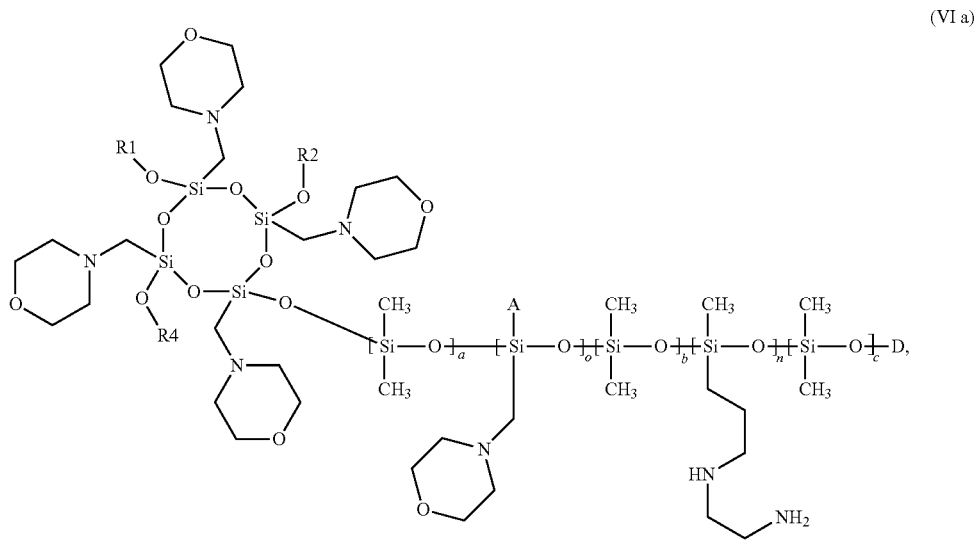

(VI a)

in which
R1, R2 and R4 independently of one another denote —H, —CH₃, a group D, a structural unit (I), (II) or (III) or an oligomeric or polymeric residue including structural units of formulae (I), (II) or (III) or two of the residues R1, R2 and R4 denote a structural unit —Si(R6)(R5)— with
R5═—CH₃ or a structural unit of formula (I) or (II) or (III) or an oligomeric or polymeric residue including structural units of formulae (I), (II) or (III)
R6═—OH, —CH₃, or a structural unit of formula (I) or (II) or (III) or an oligomeric or polymeric residue including structural units of formulae (I), (II) or (III), A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, D denotes a group —H; —Si(CH₃)₃, —Si(CH₃)₂OH, —Si(CH₃)₂OCH₃, a, b and c denote integers between 0 and 1000, with the proviso that a+b+c>0 n and o denote integers between 1 and 1000.

Further preferred silicones of formula (VI) can be described by the formula (VI b)

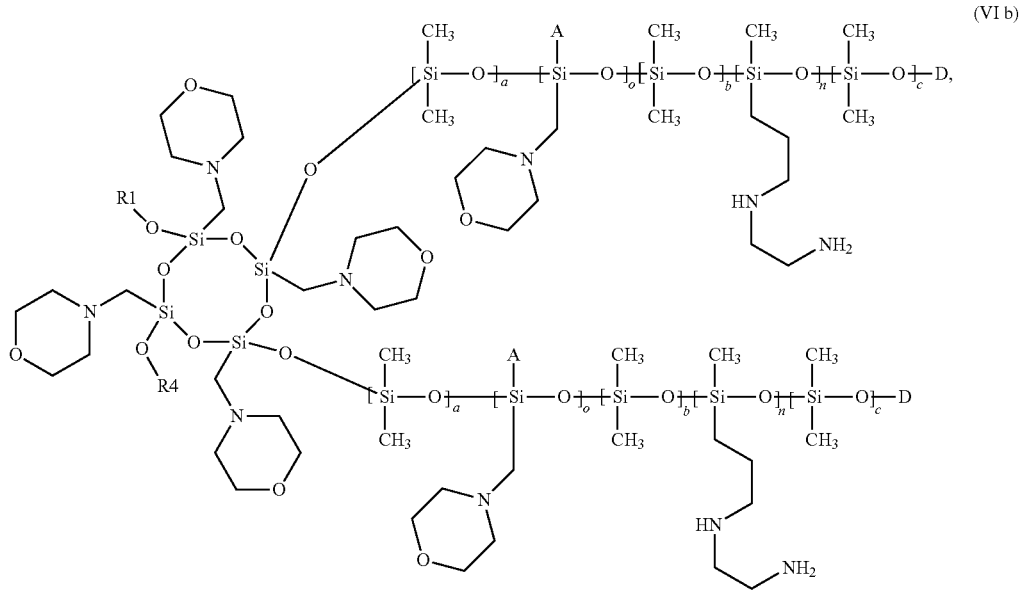

(VI b)

in which the residues and indices are as defined above.

Particularly preferred silicones of formula (VI) can be described by the formula (VI c)

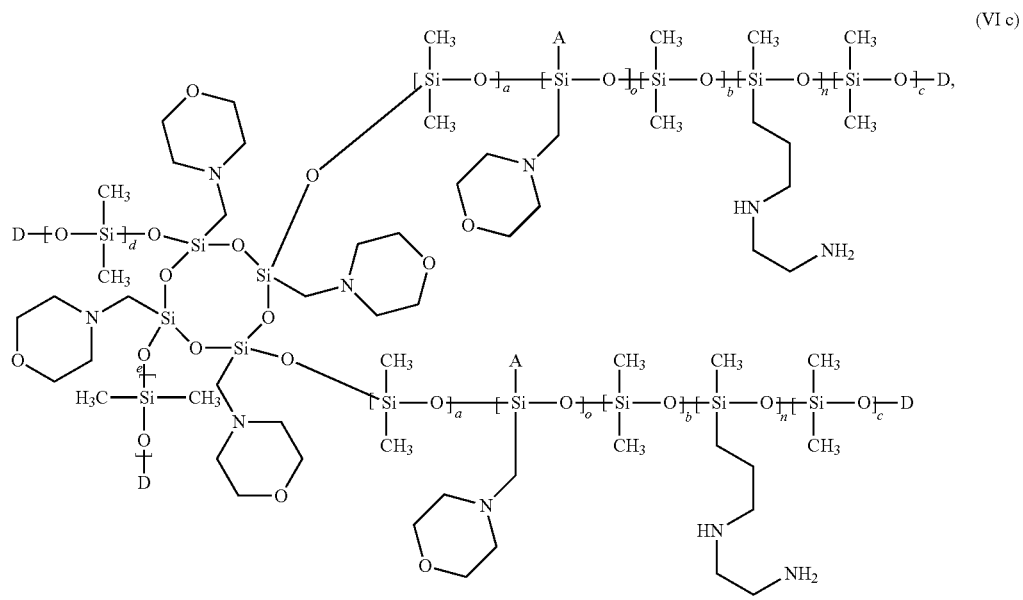

in which the residues and indices are as defined above and the indices d and e denote integers between 0 and 1000.

In formulae (VI a), (VI b) and (VI c), at least one of the groupings D preferably denotes —Si(CH$_3$)$_2$OH.

The silsequioxane structures can be even more marked in the silicones used according to the invention. Which reinforces the advantageous effects. Particularly preferred pretreatment agents according to the invention are characterized in that they include at least one 4-morpholinomethyl-substituted silicone, which comprises structural units of formula (VII)

in which
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
D denotes a group —H; —Si(CH$_3$)$_3$, —Si(CH$_3$)$_2$OH, —Si(CH$_3$)$_2$OCH$_3$,
R denotes a residue 4-morpholinomethyl,
R6 denotes —H or the grouping

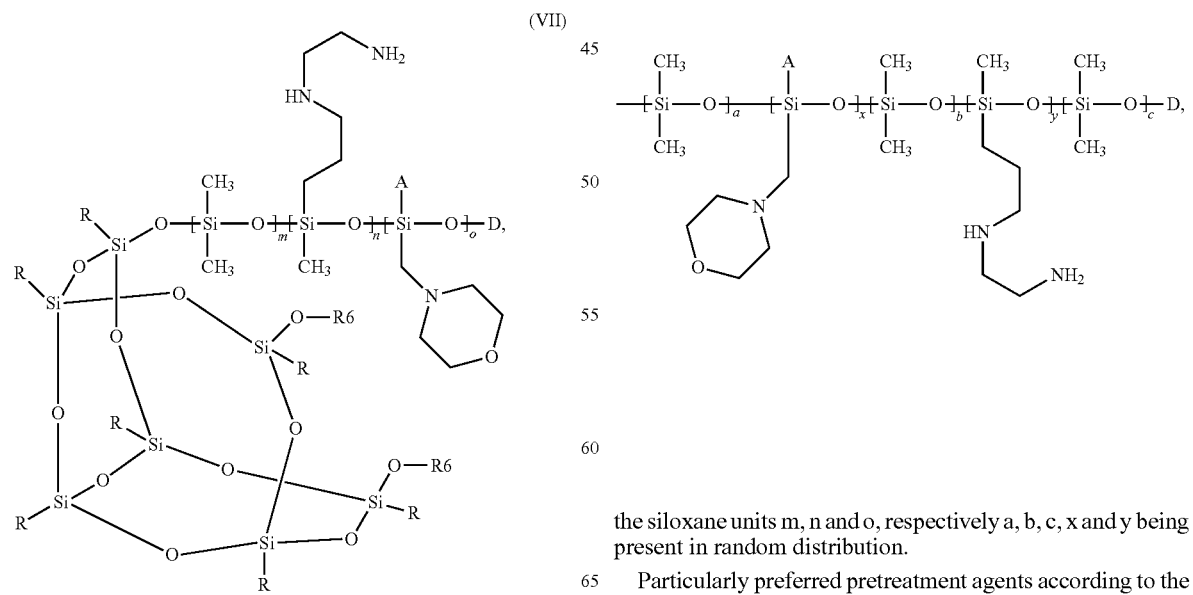

the siloxane units m, n and o, respectively a, b, c, x and y being present in random distribution.

Particularly preferred pretreatment agents according to the invention include at least one silicone of the following formula (VII a)

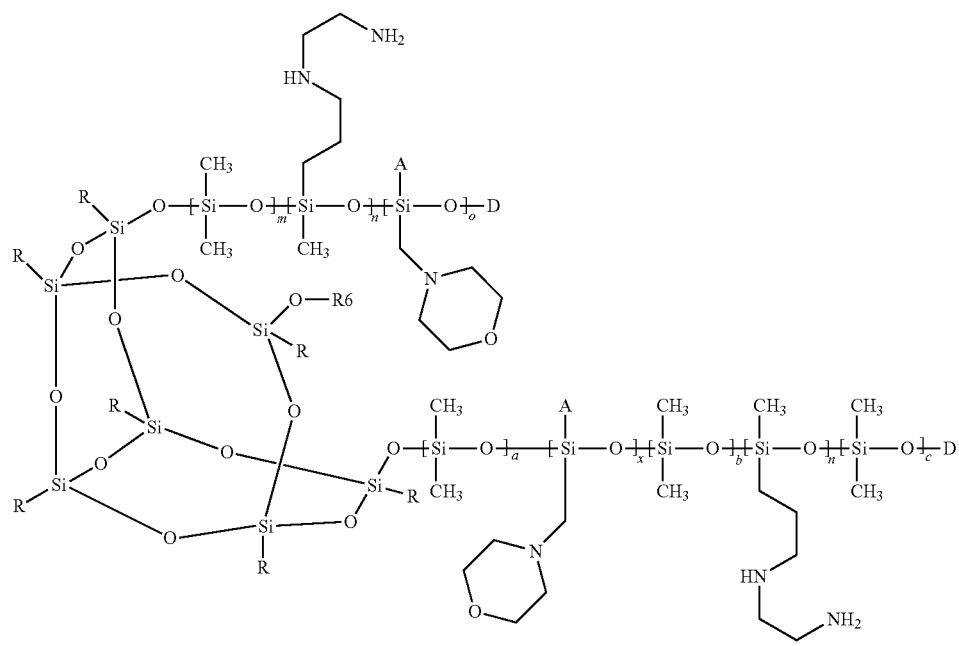
(VII a) with the definitions as for formula (VII).
Most particularly preferred pretreatment agents according to the invention include at least one silicone of the following formula (VII b)
(VIIb)
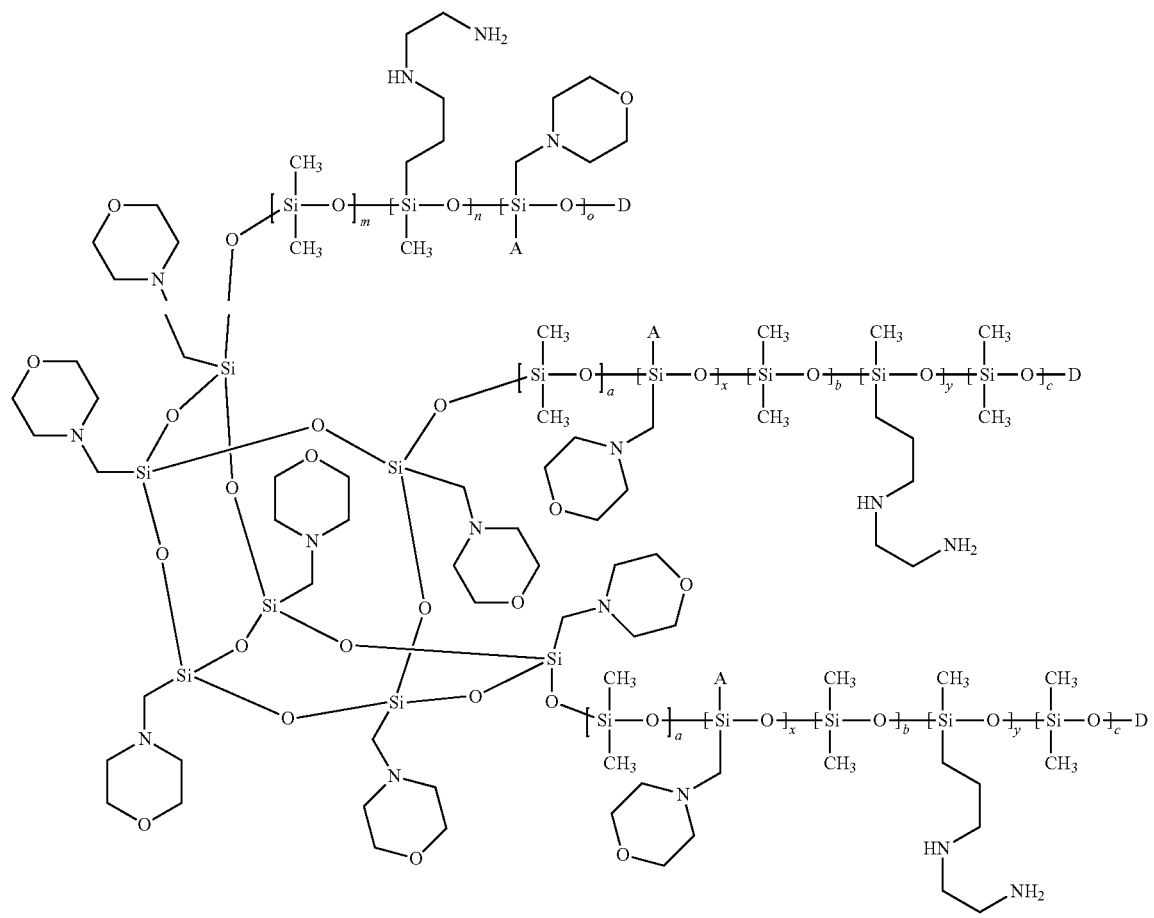

with the definitions as for formula (VII).

In formulae (VII), (VII a) and (VII b), the bridging oxygen atoms between the morpholinomethyl-substituted silicon atoms can also be extended by a —[—Si(CH$_3$)$_2$—O]$_m$ grouping, i.e. an oligomer or polymer of structural unit (I). Corresponding pretreatment agents according to the invention, including at least one 4-morpholinomethyl-substituted silicone, which comprises structural units of formula (VIII)

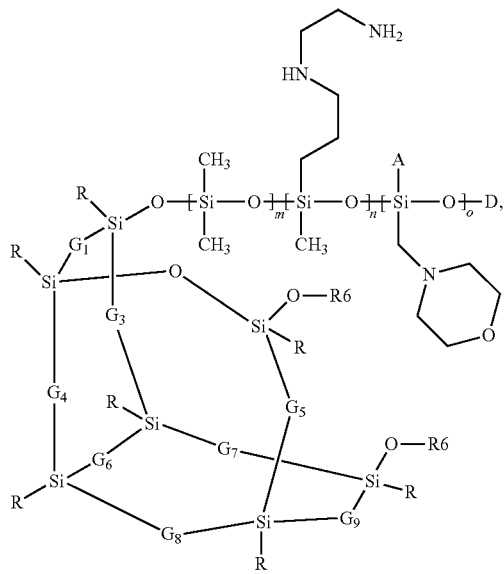

(VIII)

in which

A denotes a structural unit (I), (II) or (III) bound by an —O— or an oligomeric or polymeric residue including structural units of formulae (I), (II) or (III) bound by an —O— or half of a connecting O atom to a structural unit (III), or denotes —OH, D denotes a group —H; —Si(CH$_3$)$_3$, —Si(CH$_3$)$_2$OH, —Si(CH$_3$)$_2$OCH$_3$, G1 to G9 independently of one another denote —O— or a group —[—Si(CH$_3$)$_2$—O]$_m$— with m=1 to 200, R denotes a residue 4-morpholinomethyl, R6 denotes —H or the grouping

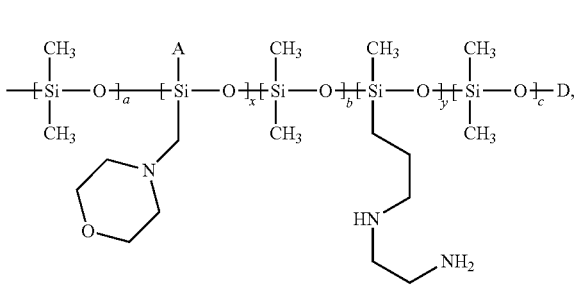

the siloxane units m, n and o, respectively a, b, c, x and y being present in random distribution.

Particularly preferred pretreatment agents according to the invention include at least one silicone of the following formula (VIII a)

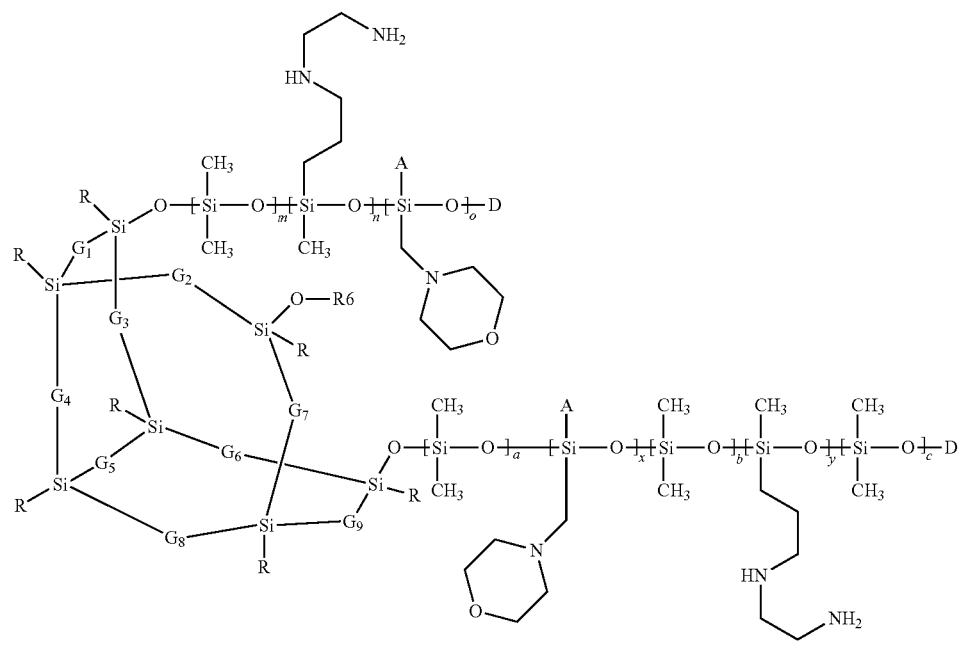

(VIII a) with the definitions as for formula (VIII).

Most particularly preferred pretreatment agents according to the invention include at least one silicone of the following formula (VIII b)

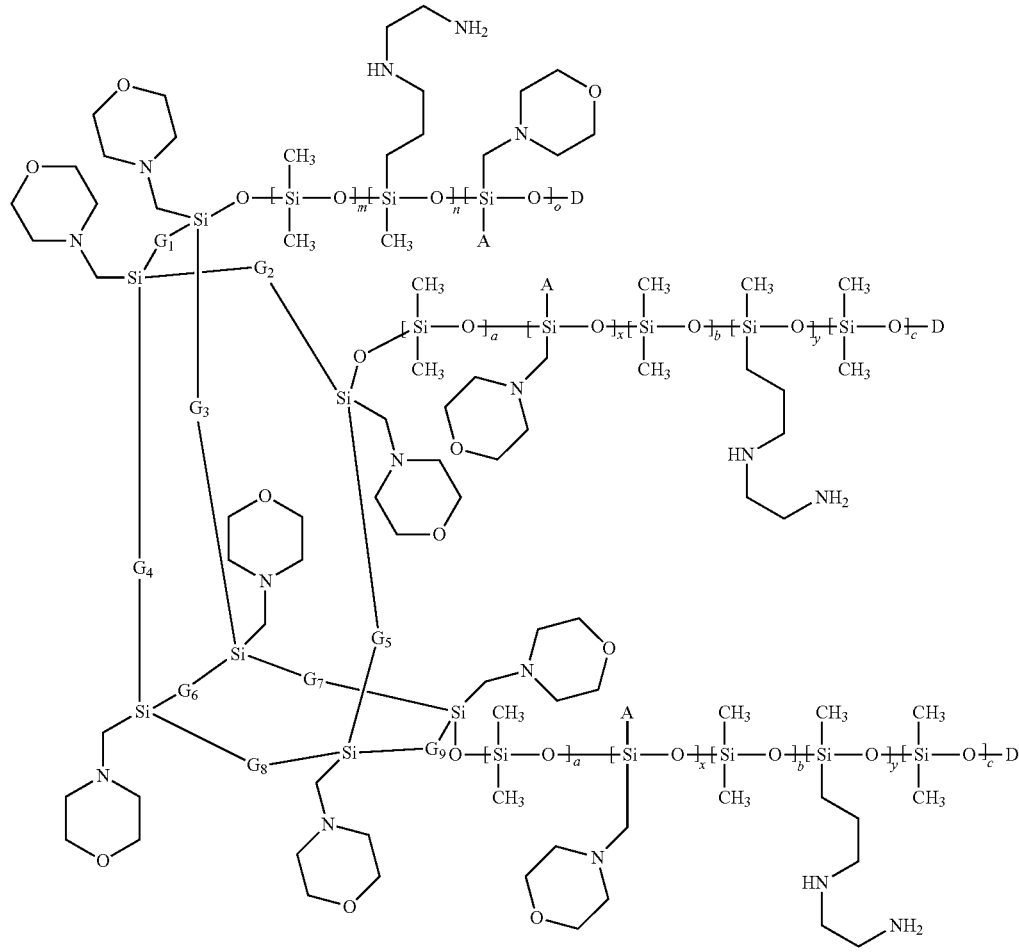

(VIII b) with the definitions as for formula (VIII).

Irrespective of which special 4-morpholinomethyl-substituted silicone is used in the pretreatment agents according to the invention, agents according to the invention including a 4-morpholinomethyl-substituted silicone in which more than 50 mole % of the structural units are dimethylsiloxy units, i.e. in which the structural unit (I) makes up at least half of all structural units in the silicone used, are preferred.

In other words, silicones are preferred in which m>(n+o) respectively (a+b+c)>(n+o) applies.

Still further preferred pretreatment agents include a 4-morpholinomethyl-substituted silicone in which more than 90 mole % of the structural units are dimethylsiloxy units, i.e. in which the structural unit (I) makes up at least nine tenths of all structural units in the silicone used.

In other words, silicones are preferred in which m>10(n+o) respectively (a+b+c)>10(n+o) applies.

Still further preferred pretreatment agents include a 4-morpholinomethyl-substituted silicone in which more than 98 mole % of the structural units are dimethylsiloxy units, i.e. in which the structural unit (I) makes up at least ninety-eight hundredths of all structural units in the silicone used.

In other words, silicones are preferred in which m>50(n+o) respectively (a+b+c)>50(n+o) applies.

Still further preferred hair treatment agents include a 4-morpholinomethyl-substituted silicone in which more than 98.5 mole % of the structural units are dimethylsiloxy units, i.e. in which the structural unit (I) makes up at least nine hundred and eight-five thousandths of all structural units in the silicone used.

In other words, silicones are preferred in which m>75(n+o) respectively (a+b+c)>75(n+o) applies.

Still further preferred pretreatment agents include a 4-morpholinomethyl-substituted silicone in which more than 99 mole % of the structural units are dimethylsiloxy units, i.e. in which the structural unit (I) makes up at least nine tenths of all structural units in the silicone used. In other words, silicones are preferred in which m>100(n+o) respectively (a+b+c) >100(n+o) applies.

In summary, preferred pretreatment agents according to the invention are characterized in that they include at least one 4-morpholinomethyl-substituted silicone, in which:
- m>(n+o) respectively (a+b+c)>(n+o), preferably
- m>10(n+o) respectively (a+b+c)>10(n+o), particularly preferably
- m>50(n+o) respectively (a+b+c)>50(n+o), more preferably
- m>75(n+o) respectively (a+b+c)>75(n+o) and in particular
- m>100(n+o) respectively (a+b+c)>100(n+o).

The 4-morpholinomethyl-substituted silicone(s) can be used in varying quantities depending on the intended application of the agents according to the invention. Preferred pretreatment agents according to the invention are characterized in that they include—based on their weight—0.00001 to 10 wt. %, preferably 0.0001 to 7.5 wt. %, particularly preferably 0.001 to 5 wt. %, more preferably 0.01 to 3 wt. % and in particular 0.1 to 1 wt. % 4-morpholinomethyl-substituted silicone(s).

It has been shown that the action of the silicones used according to the invention can be increased still further if specific nonionic components are also used in the agents according to the invention. Moreover, these nonionic components have positive effects on the storage stability of the agents according to the invention. Nonionic components that are particularly suitable here are ethoxylates of decanol, undecanol, dodecanol, tridecanol etc. Ethoxylated tridecanols, which are incorporated into the agents according to the invention with particular preference, have proved particularly suitable. Particularly preferred pretreatment agents according to the invention include—based on their weight—0.00001 to 5 wt. %, preferably 0.0001 to 3.5 wt. %, particularly preferably 0.001 to 2 wt. %, more preferably 0.01 to 1 wt. % and in particular 0.1 to 0.5 wt. % branched, ethoxylated tridecanol (INCI name: Trideceth-5) or α-isotridecyl-ω-hydroxy polyglycol ether (INCI name: Trideceth-10) or mixtures thereof.

Other surfactants and emulsifiers are preferably not included in the agents according to the invention or are included only in small quantities. Preferred agents according to the invention are formulated to be low in surfactants, wherein preferred agents include ≤5 wt. % surfactant(s), preferably ≤2.5 wt. % surfactant(s), more preferably ≤1 wt. % surfactant(s) and in particular ≤0.5 wt. % surfactant(s).

The compounds of formula (II) are included in calculating this quantity of surfactant.

The agents according to the invention are preferably formulated with low viscosity. Moreover, it has been shown that thickening polymers can reduce the action according to the invention, and so preferred agents according to the invention are characterized in that they include ≤2.5 wt. %, preferably ≤1 wt. %, more preferably ≤0.5 wt. % and in particular ≤0.01 wt. % thickening polymer(s).

With particular preference, the agents according to the invention include, irrespective of the special action of the polymer(s), ≤2.5 wt. %, preferably ≤1 wt. %, more preferably ≤0.5 wt. % and in particular ≤0.01 wt. % synthetic polymer(s).

The pretreatment agents according to the invention can include other ingredients. Preferred here is the use of polyhydric alcohols having moisture-donating properties. In this case, agents according to the invention are preferred which include—based on their weight—0.05 to 15 wt. %, preferably 0.1 to 10 wt. %, particularly preferably 0.15 to 5 wt. % and in particular 0.15 to 1 wt. % of at least one polyhydric alcohol from the group of sorbitol and/or glycerol and/or 1,2-propylene glycol.-% or mixtures thereof.

For specific areas of application it can be advantageous to use only one of the three above-mentioned ingredients. In most cases, glycerol is preferred. In other areas of application, however, mixtures of two of the three substances or of all three substances can be preferred. A mixture of glycerol, sorbitol and 1,2-propylene glycol in a weight ratio of 1:(0.5-1):(0.1-0.5) has proved particularly advantageous here.

In addition to sorbitol or glycerol or 1,2-propylene glycol, other polyhydric alcohols that are suitable are those with at least 2 OH groups, preferably mannitol, xylitol, polyethylene glycol, polypropylene glycol and mixtures thereof. Among these compounds, those with 2 to 12 OH groups and in particular those with 2, 3, 4, 5, 6 or 10 OH groups are preferred.

Polyhydroxy compounds with 2 OH groups are e.g. glycol ($CH_2(OH)CH_2OH$) and other 1,2-diols, such as $H-(CH_2)_n-CH(OH)CH_2OH$ with n=2, 3, 4, 5, 6, 7, 8, 9, 10, 11, 12, 13, 14, 15, 16, 17, 18, 19, 20. 1,3-Diols, such as $H-(CH_2)_n-CH(OH)CH_2CH_2OH$ with n=1, 2, 3, 4, 5, 6, 7, 8, 9, 10, 11, 12, 13, 14, 15, 16, 17, 18, 19, 20, can also be used according to the invention. The (n,n+1) or (n,n+2)diols with non-terminal OH groups can also be used. Important representatives of polyhydroxy compounds with 2 OH groups are also polyethylene and polypropylene glycols. As preferred other polyhydric alcohols, e.g. xylitol, propylene glycols, polyethylene glycols, in particular those with average molecular weights of 200-800, can be used.

Particularly preferred is the use of glycerol, and so agents that include no other polyhydric alcohols apart from glycerol are particularly preferred.

With regard to pretreatment before an oxidative treatment, the use of specific care substances in the agents according to the invention is preferred.

Preferred pretreatment agents according to the invention are characterized in that they additionally include care substance(s)—based on their weight—in quantities of 0.001 to 10 wt. %, preferably 0.005 to 7.5 wt. %, particularly preferably 0.01 to 5 wt. % and in particular 0.05 to 2.5 wt. %, preferred care substance(s) being selected from the group of
  i. L-carnitine and/or salts thereof;
  ii. taurine and/or salts thereof;
  iii. niacinamide;
  iv. ubiquinone
  v. ectoine.

L-Carnitine (IUPAC name (R)-(3-carboxy-2-hydroxypropyl)-N,N,N-trimethylammonium hydroxide) is a naturally occurring, vitamin-like substance. As a betaine, L-carnitine can form addition compounds and double salts. Preferred L-carnitine derivatives according to the invention are selected in particular from acetyl L-carnitine, L-carnitine fumarate, L-carnitine citrate, lauroyl L-carnitine and particularly preferably L-carnitine tartrate. The aforementioned L-carnitine compounds are available e.g. from Lonza GmbH (Wuppertal, Germany).

Preferred hair treatment agents according to the invention are characterized in that they include—based on their weight—0.001 to 10 wt. %, preferably 0.005 to 7.5 wt. %, particularly preferably 0.01 to 5 wt. % and in particular 0.05 to 2.5 wt. % L-carnitine or L-carnitine derivatives, preferred L-carnitine derivatives being selected from acetyl L-carnitine, L-carnitine fumarate, L-carnitine citrate, lauroyl L-carnitine and in particular L-carnitine tartrate.

Another preferred care substance that can be used is taurine. Preferred hair treatment agents according to the invention include—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % taurine (2-aminoethanesulfonic acid).

Another preferred group of care substances in the agents according to the invention are vitamins, provitamins or vitamin precursors. These are described below:

The group of substances referred to as vitamin A includes retinol (vitamin $A_1$) and 3,4-didehydroretinol (vitamin $A_2$). β-Carotene is the provitamin of retinol. Suitable according to the invention as vitamin A component are e.g. vitamin A acid and esters thereof, vitamin A aldehyde and vitamin A alcohol and esters thereof, such as the palmitate and the acetate. The agents according to the invention include the vitamin A component preferably in quantities of 0.05-1 wt. %, based on the overall preparation.

The vitamin B group or vitamin B complex includes, inter alia:
  Vitamin $B_1$ (thiamine)
  Vitamin $B_2$ (riboflavin)
  Vitamin $B_3$. This name often covers the compounds nicotinic acid and nicotinamide (niacinamide). Preferred according to the invention is nicotinamide, which is included in the agents used according to the invention preferably in quantities of 0.05 to 1 wt. %, based on the overall agent.
  Vitamin $B_5$ (pantothenic acid, panthenol and pantolactone). Within the framework of this group, preferably panthenol and/or pantolactone is used (see below). Derivatives of panthenol that can be used according to the invention are in particular the esters and ethers of panthenol and cationically derivatized panthenols. The aforementioned compounds of the vitamin $B_5$ type are included in the agents according to the invention preferably in quantities of 0.05-10 wt. %, based on the overall agent. Quantities of 0.1-5 wt. % are particularly preferred.

Vitamin $B_6$ (pyridoxine as well as pyridoxamine and pyridoxal).

Vitamin C (ascorbic acid). Vitamin C is used in the agents according to the invention preferably in quantities of 0.1 to 3 wt. %, based on the overall agent.

Vitamin E (tocopherols, in particular α-tocopherol). Tocopherol and derivatives thereof, including in particular the esters, such as the acetate, the nicotinate, the phosphate and the succinate, are included in the agents according to the invention preferably in quantities of 0.05-1 wt. %, based on the overall agent.

Vitamin F. The term "vitamin F" is generally understood to mean essential fatty acids, in particular linoleic acid, linolenic acid and arachidonic acid.

Vitamin H. The compound (3aS,4S,6aR)-2-oxohexahydrothieno[3,4-d]-imidazole-4-valeric acid is referred to as vitamin H, but its trivial name biotin has now become accepted. Biotin is included in the agents according to the invention preferably in quantities of 0.0001 to 1.0 wt. %, in particular in quantities of 0.001 to 0.01 wt. %.

In summary, hair treatment agents according to the invention are preferred which include—based on their weight—0.1 to 5 wt. %, preferably 0.2 to 4 wt. %, particularly preferably 0.25 to 3.5 wt. %, more preferably 0.5 to 3 wt. % and in particular 0.5 to 2.5 wt. % vitamins and/or pro-vitamins and/or vitamin precursors, which preferably belong to the groups A, B, C, E, F and H, wherein preferred agents include -2,4-dihydroxy-N-(3-hydroxypropyl)-3,3-dimethylbutyramide, provitamin $B_5$) and/or pantothenic acid (vitamin $B_3$, vitamin $B_5$) and/or niacin, niacinamide or nicotinamide (vitamin $B_3$) and/or L-ascorbic acid (vitamin C) and/or thiamine (vitamin $B_1$) and/or riboflavin (vitamin $B_2$, vitamin G) and/or biotin (vitamin $B_7$, vitamin H) and/or folic acid (vitamin $B_9$, vitamin $B_c$ or vitamin M) and/or vitamin $B_6$ and/or vitamin $B_{12}$.

It has been shown that specific quinones have a particular suitability as a care substance. As an additional care substance, the agents according to the invention can therefore include 0.0001 to 5 wt. % of at least one bioquinone of the formula (Ubi)

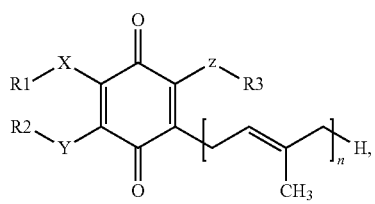

(Ubi)

in which
X, Y, Z independently of one another denote —O— or —NH— or $NR^4$— or a chemical bond
$R^1$, $R^2$, $R^3$ independently of one another denote a hydrogen atom or an optionally substituted aryl group or an optionally substituted ($C_1$-$C_6$)alkyl group or a hydroxyalkyl group or a polyhydroxyalkyl group or an optionally substituted ($C_1$-$C_6$)alkylene group or a ($C_1$-$C_6$) acyl residue, wherein preferred residues are selected independently of one another from —H, —$CH_3$, —$CH_2CH_3$, —$(CH_2)_2CH_3$, —$CH(CH_3)_2$, —$(CH_2)_3CH_3$, —$CH(CH_3)CH_2CH_3$, —$CH_2CH(CH_3)_2$, —$C(CH_3)_3$
$R^4$ denotes —$CH_3$, —$CH_2CH_3$, —$(CH_2)_2CH_2$, —$CH(CH_3)_2$, —$(CH_2)_3CH_3$, —$CH(CH_3)CH_2CH_3$, —$CH_2CH(CH_3)_2$, —$C(CH_3)_3$ n denotes values of 1 to 20, preferably of 2 to 15 and in particular denotes 5, 6, 7, 8, 9, 10.

Particularly preferred pretreatment agents according to the invention are characterized in that they include as care substance—based on their weight—0.0001 to 1 wt. %, preferably 0.001 to 0.5 wt. % and particularly preferably 0.005 to 0.1 wt. % of at least one ubiquinone and/or of at least one ubiquinol and/or of at least one derivative of these substances, wherein preferred agents include an ubiquinone of the formula (Ubi)

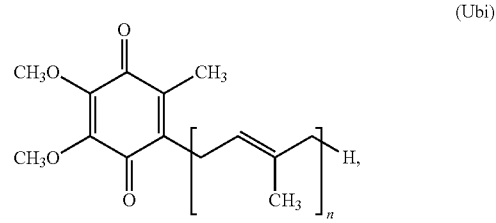

(Ubi)

in which n denotes the values=6, 7, 8, 9 or 10, particularly preferably 10 (coenzyme Q10).

Alternatively to the particularly preferred ubiquinones or in addition thereto, the agents according to the invention can also include plastoquinones. In this case, preferred agents according to the invention are characterized in that they include 0.0002 to 4 wt. %, preferably 0.0005 to 3 wt. %, particularly preferably 0.001 to 2 wt. %, more preferably 0.0015 to 1 and in particular 0.002 to 0.5 wt. % of at least one plastoquinone of the formula (Ubi-b)

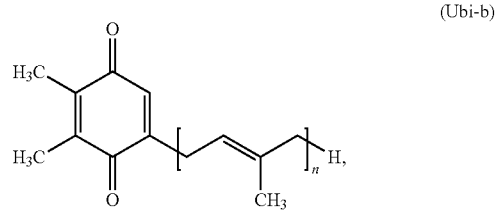

(Ubi-b)

in which n denotes values of 1 to 20, preferably of 2 to 15 and in particular 5, 6, 7, 8, 9, 10, wherein agents particularly preferably include plastoquinone PQ-9 of the formula

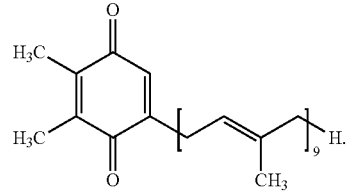

As an additional care substance, the agents according to the invention can include ectoine ((4S)-2-methyl-1,4,5,6-tetrahydropyrimidine-4-carboxylic acid). Preferred pretreatment agents according to the invention are characterized in that they include—based on their weight—0.001 to 10 wt. %, preferably 0.01 to 5 wt. %, particularly preferably 0.05 to 2.5 wt. % and in particular 0.1 to 1 wt. % (S)-2-methyl-1,4,5,6-tetrahydro-4-pyrimidinecarboxylic acid (ectoine) and the physiologically acceptable salts of this compound and/or (S,S)-5-hydroxy-2-methyl-1,4,5,6-tetrahydro-4-pyrimidinecarboxylic acid (hydroxyectoine) and the physiologically acceptable salts of this compound.

To improve the elasticity and strengthen the internal structure of hair that has been pretreated with agents according to the invention, the agents according to the invention can include purine and/or purine derivatives as care substance. In particular the combination of purine and/or purine derivatives with ubiquinones and/or plastoquinones as care substance leads to a damage-free outcome from the subsequent oxidative treatment.

Purine (7H-imidazo[4,5-d]pyrimidine) does not occur in free form in nature but forms the parent substance of the purines. Purines themselves are a group of important compounds which are widespread in nature and take part in human, animal, plant and microbial metabolic processes and are derived from the parent substance by substitution with OH, $NH_2$, SH in 2-, 6- and 8-position and/or with $CH_3$ in 1-, 3-, 7-position. Purine can be produced e.g. from aminoacetonitrile and formamide. Purines and purine derivatives are often isolated from natural substances, but can also be produced synthetically by many routes.

Preferred agents according to the invention include purine and/or purine derivatives in relatively narrow quantitative ranges. In this case, preferred agents according to the invention are characterized in that they include—based on their weight—0.001 to 2.5 wt. %, preferably 0.0025 to 1 wt. %, particularly preferably 0.005 to 0.5 wt. % and in particular 0.01 to 0.1 wt. % purine(s) and/or purine derivative(s).

Some representatives of purine, the purines and the purine derivatives are particularly preferred according to the invention. Preferred pretreatment agents according to the invention are characterized in that they include as care substance—based on their weight—0.001 to 2.5 wt. %, preferably 0.0025 to 1 wt. %, particularly preferably 0.005 to 0.5 wt. % and in particular 0.01 to 0.1 wt. % purine(s) and/or purine derivative(s), wherein preferred agents include purine and/or purine derivative(s) of the formula (Pur-I)

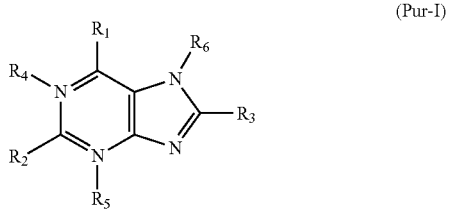
(Pur-I)

in which the residues $R^1$, $R^2$ and $R^3$, independently of one another, are selected from —H, —OH, $NH_2$, —SH and the residues $R^4$, $R^5$ and $R^6$, independently of one another, are selected from —H, —$CH_3$ and —$CH_2$—$CH_3$, wherein the following compounds are preferred:
  purine ($R^1$=$R^2$=$R^3$=$R^4$=$R^5$=$R^6$=H)
  adenine ($R^1$=$NH_2$, $R^2$=$R^3$=$R^4$=$R^5$=$R^6$=H)
  guanine ($R^1$=OH, $R^2$=$NH_2$, $R^3$=$R^4$=$R^5$=$R^6$=H)
  uric acid ($R^1$=$R^2$=$R^3$=OH, $R^4$=$R^5$=$R^6$=H)
  hypoxanthine ($R^1$=OH, $R^2$=$R^3$=$R^4$=$R^5$=$R^6$=H)
  6-purinethiol ($R^1$=SH, $R^2$=$R^3$=$R^4$=$R^5$=$R^6$=H)
  6-thioguanine ($R^1$=SH, $R^2$=$NH_2$, $R^3$=$R^4$=$R^5$=$R^6$=H)
  xanthine ($R^1$=$R^2$=OH, $R^3$=$R^4$=$R^5$=$R^6$=H)
  caffeine ($R^1$=$R^2$=OH, $R^3$=H, $R^4$=$R^5$=$R^6$=$CH_3$)
  theobromine ($R^1$=$R^2$=OH, $R^3$=$R^4$=H, $R^5$=$R^6$=$CH_3$)
  theophylline ($R^1$=$R^2$=OH, $R^3$=H, $R^4$=$CH_3$, $R^5$=$CH_3$, $R^6$=H).

It is furthermore advantageous to use purine or purine derivatives and bioquinones in a specific ratio to one another. In this case, agents according to the invention are preferred in which the weight ratio of purine (derivative(s)) and bioquinone(s) is 10:1 to 1:100, preferably 5:1 to 1:50, particularly preferably 2:1 to 1:20 and in particular 1:1 to 1:10.

As already mentioned, caffeine is a particularly preferred purine derivative and coenzyme Q10 is a particularly preferred bioquinone. Particularly preferred agents according to the invention are therefore characterized in that they include—based on their weight—0.001 to 2.5 wt. %, preferably 0.0025 to 1 wt. %, particularly preferably 0.005 to 0.5 wt. % and in particular 0.01 to 0.1 wt. % caffeine and 0.0002 to 4 wt. %, preferably 0.0005 to 3 wt. %, particularly preferably 0.001 to 2 wt. %, more preferably 0.0015 to 1 and in particular 0.002 to 0.5 wt. % coenzyme Q10.

As care substance, the agents according to the invention can also include flavonoids. The flavonoids are a group of water-soluble plant dyes and play an important part in the metabolism of many plants. Together with the phenolic acids, they belong to the polyphenols. Well in excess of 6500 different flavonoids are known, which can be divided into flavonols, flavones, flavanones, isoflavonoids and anthocyans.

According to the invention, flavonoids from all six groups can be used, with specific representatives of the individual groups being preferred as care substance owing to their particularly intensive action. Preferred flavonols are quercetin, rutin, kaempferol, myricetin, isorhamnetin, preferred flavanols are catechin, gallocatechin, epicatechin, epigallocatechin gallate, theaflavin, thearubigin, preferred flavones are luteolin, apigenin, morin, preferred flavanones are hesperetin, naringenin, eriodictyol, preferred isoflavonoids are genistein, daidzein, and preferred anthocyanidins (anthocyans) are cyanidin, delphinidin, malvidin, pelargonidin, peonidin, petunidin.

Particularly preferred pretreatment agents according to the invention are characterized in that they include—based on their weight—0.001 to 2.5 wt. %, preferably 0.0025 to 1 wt. %, particularly preferably 0.005 to 0.5 wt. % and in particular 0.01 to 0.1 wt. % flavonoids, in particular flavonols, particularly preferably 3,3',4',5,7-pentahydroxyflavone (quercetin) and/or 3,3',4',5,7-pentahydroxyflavone-3-O-rutinoside (rutin).

Also preferred is the use of bisabolol and/or bisabolol oxides as care substance in the agents according to the invention. In this case, pretreatment agents according to the invention are preferred which additionally include 0.001 to 5 wt. %, preferably 0.01 to 4 wt. %, particularly preferably 0.02 to 2.5 wt. % and in particular 0.1 to 1.5 wt. % bisabolol and/or oxides of bisabolol, preferably (–)-alpha-bisabolol.

Creatine is also suitable according to the invention as a care substance. Creatine (3-methylguanidinoacetic acid) is an organic acid, which inter alia contributes to supplying energy to the muscles in vertebrates. Creatine is synthesized in the kidney, liver and pancreas. It is formally derived from the amino acids glycine and arginine and 95% of it is located in skeletal muscle. Particularly preferred pretreatment agents according to the invention include—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % N-methylguanidinoacetic acid (creatine).

In addition to the care substances, the agents according to the invention can include other care substances. Their presence is not absolutely essential to achieve the effects according to the invention, but additional effects, such as a pleasant handle or pleasant application feel, can result from the use of these care substances.

As a further ingredient, the agents according to the invention can, with particular preference, include one or more amino acids. Amino acids that can be particularly preferably used according to the invention come from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-Dopa), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine and L-ornithine, it being possible to use both the individual amino acids and mixtures.

Preferred agents according to the invention include one or more amino acids in relatively narrow quantitative ranges. In this case, preferred hair treatment agents according to the invention are characterized in that they include as care substance—based on their weight—0.01 to 5 wt. %, preferably 0.02 to 2.5 wt. %, particularly preferably 0.05 to 1.5 wt. %, more preferably 0.075 to 1 wt. % and in particular 0.1 to 0.25 wt. % amino acid(s), preferably from the group of glycine and/or alanine and/or valine and/or lysine and/or leucine and/or threonine.

As a further constituent, the agents according to the invention can include at least one carbohydrate from the group of the monosaccharides, disaccharides and/or oligosaccharides. In this case, preferred hair treatment agents according to the invention are characterized in that they include as care substance—based on their weight—0.01 to 5 wt. %, preferably 0.05 to 4.5 wt. %, particularly preferably 0.1 to 4 wt. %, more preferably 0.5 to 3.5 wt. % and in particular 0.75 to 2.5 wt. % carbohydrate(s), selected from monosaccharides, disaccharides and/or oligosaccharides, wherein preferred carbohydrates are selected from monosaccharides, in particular D-ribose and/or D-xylose and/or L-arabinose and/or D-glucose and/or D-mannose and/or D-galactose and/or D-fructose and/or sorbose and/or L-fucose and/or L-rhamnose as well as disaccharides, in particular sucrose and/or maltose and/or lactose and/or trehalose and/or cellobiose and/or gentiobiose and/or isomaltose.

Particularly preferred agents according to the invention include, based on their weight,
    0.005 to 0.015 wt. % caffeine and 0.75 to 1.5 wt. % glucose monohydrate,
    0.005 to 0.015 wt. % caffeine and 0.75 to 1.5 wt. % sucrose,
    0.005 to 0.015 wt. % caffeine and 0.75 to 1.5 wt. % fructose.

As already mentioned, preferred agents according to the invention include (an) amino acid(s).

Amino acids that can be used particularly preferably according to the invention come from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-Dopa), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, it being possible to use both the individual amino acids and mixtures.

Preferred agents according to the invention include one or more amino acids in relatively narrow quantitative ranges. In this case, preferred agents according to the invention are characterized in that they additionally include—0.05 to 5 wt. %, preferably 0.1 to 2.5 wt. %, particularly preferably 0.15 to 1 wt. % and in particular 0.2 to 0.5 wt. % amino acid(s), preferably (an) amino acid(s) from the group of glycine and/or alanine and/or valine and/or lysine and/or leucine and/or threonine.

Particularly preferred agents according to the invention include, based on their weight,
    0.005 to 0.015 wt. % caffeine and 0.75 to 1.5 wt. % glucose monohydrate and 0.1 to 0.25 wt. % glycine,
    0.005 to 0.015 wt. % caffeine and 0.75 to 1.5 wt. % sucrose and 0.1 to 0.25 wt. % glycine,
    0.005 to 0.015 wt. % caffeine and 0.75 to 1.5 wt. % fructose and 0.1 to 0.25 wt. % glycine,
    0.005 to 0.015 wt. % caffeine and 0.75 to 1.5 wt. % glucose monohydrate and 0.1 to 0.25 wt. % alanine,
    0.005 to 0.015 wt. % caffeine and 0.75 to 1.5 wt. % sucrose and 0.1 to 0.25 wt. % alanine,
    0.005 to 0.015 wt. % caffeine and 0.75 to 1.5 wt. % fructose and 0.1 to 0.25 wt. % alanine,
    0.005 to 0.015 wt. % caffeine and 0.75 to 1.5 wt. % glucose monohydrate and 0.1 to 0.25 wt. % valine,
    0.005 to 0.015 wt. % caffeine and 0.75 to 1.5 wt. % sucrose and 0.1 to 0.25 wt. % valine,
    0.005 to 0.015 wt. % caffeine and 0.75 to 1.5 wt. % fructose and 0.1 to 0.25 wt. % valine.

The present invention also provides a method for oxidative hair treatment, in which
    a) a pretreatment agent according to the invention is applied onto the keratinic fibers,
    b) the keratinic fibers are subjected to an oxidative hair treatment within a period of one second to 24 hours after step a).

The method according to the invention encompasses the application of a pretreatment agent onto keratinic fibers and a subsequent oxidative treatment. A great advantage of the agents used in step a) is that they are effective not only if they are applied immediately before the oxidative treatment, but can be applied up to 24 hours in advance without the risk of the effect being reduced by external influences. In this way, it is possible to carry out step a) of the method according to the invention for example in the morning after washing the hair and the oxidative treatment not until the evening.

An oxidative hair treatment can serve to change the color and/or shape of keratinic fibers. In the case of a change in shape (permanent wave, straightening), the hair is treated with another agent prior to the oxidative treatment (fixing) in order to make the fiber structure malleable. In preferred methods according to the invention, the oxidative treatment serves to change the color, i.e. it represents lightening ("blonding") or dyeing.

Preferred methods according to the invention are characterized in that step b) encompasses the application of an agent for blonding human hair, which includes at least one peroxo compound that is selected from hydrogen peroxide and its addition compounds on solid carriers, ammonium and alkali metal persulfates and peroxydisulfates.

In the blonding agent used in step b) of the method according to the invention, hydrogen peroxide is included. Hydrogen peroxide is preferably used itself as an aqueous solution. However, the hydrogen peroxide can also be used in the form of a solid addition compound of hydrogen peroxide to inorganic or organic compounds, such as e.g. sodium perborate, sodium percarbonate, magnesium percarbonate, sodium percarbamide, polyvinylpyrrolidone n $H_2O_2$ (n is a positive integer greater than 0), urea peroxide and melamine peroxide.

Most particularly preferred according to the invention are aqueous hydrogen peroxide solutions. The concentration of a hydrogen peroxide solution is determined on the one hand by the legal requirements and on the other hand by the desired effect; preferably 6 to 12% solutions in water are used. Preferred methods according to the invention are characterized in that the agents used in step b) include—based on their weight—0.5 to 12 wt. %, preferably 2 to 10 wt. %, particularly preferably 3 to 6 wt. % hydrogen peroxide (calculated as 100% $H_2O_2$).

Blonding processes on keratin fibers generally take place in an alkaline medium. To protect the keratin fibers and the skin as far as possible, however, it is not desirable to establish too high a pH value. It is therefore preferred if the pH value of the agent used in step b) is between 7 and 11, in particular between 8 and 10.5.

The pH values within the meaning of the present invention are pH values that were measured at a temperature of 22° C.

The alkalizing agents that can be used according to the invention to establish the preferred pH value can be selected from the group of ammonia, basic amino acids, alkali hydroxides, alkanolamines, alkali metal metasilicates, alkali phosphates and alkali hydrogen phosphates. Lithium, sodium, potassium, in particular sodium or potassium, are preferably used as alkali metal ions.

The basic amino acids that can be used as alkalizing agents are preferably selected from the group of L-arginine, D-arginine, D,L-arginine, L-lysine, D-lysine, D,L-lysine, particularly preferably L-arginine, D-arginine, D,L-arginine as an alkalizing agent within the meaning of the invention.

The alkali hydroxides that can be used as alkalizing agents are preferably selected from the group of sodium hydroxide and potassium hydroxide.

The alkanolamines that can be used as alkalizing agents are preferably selected from primary amines with a $C_2$-$C_6$ alkyl parent substance, carrying at least one hydroxyl group. Particularly preferred alkanolamines are selected from the group that is made up of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Most particularly preferred alkanolamines according to the invention are selected from the group of 2-aminoethan-1-ol, 2-amino-2-methylpropan-1-ol and 2-amino-2-methylpropane-1,3-diol.

For the intense lightening of very dark hair, the use of hydrogen peroxide or addition products thereof to organic or inorganic compounds is often insufficient. In these cases, a combination of hydrogen peroxide and persulfates is generally used.

The persulfate salts can be included in a quantity of 0.1 to 25 g, in particular in a quantity of 1 to 15 g, based on 100 g of the ready-to-use agent.

Preferred persulfate salts are ammonium peroxydisulfate, potassium peroxydisulfate, sodium peroxydisulfate, ammonium persulfate, potassium persulfate and sodium persulfate.

Alternatively, the method according to the invention can also be used in hair dyeing. In these preferred embodiments, the method according to the invention is characterized in that step b) encompasses the application of a hair coloring agent, which includes at least one oxidation dye precursor and at least one oxidizing agent.

As a first essential ingredient, the agents used in step b) of this method according to the invention therefore include at least one oxidation dye precursor.

Oxidation dye precursors can be divided into two categories on the basis of their reaction behavior, so-called developer components and coupler components.

Developer components can form the actual dye by themselves. They can therefore be included in the agent according to the invention as sole color-changing compounds. In a preferred embodiment, the agents according to the invention include at least one oxidation dye precursor of the developer type and/or coupler type. The coloring agents according to the invention preferably include at least one oxidation dye precursor of the developer type and at least one oxidation dye precursor of the coupler type.

The developer and coupler components are generally used in free form. However, in the case of substances with amino groups it can be preferred to use them in salt form, particularly in the form of the hydrochlorides and hydrobromides or sulfates.

Particularly preferred developer components are selected from at least one compound from the group made up of p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,1-bis(2,5-di aminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts of these compounds.

Most particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and physiologically acceptable salts thereof.

The developer components are used preferably in a quantity of 0.005 to 20 wt. %, preferably 0.1 to 5 wt. %, based in each case on the ready-to-use oxidation coloring agent.

Coupler components do not form any significant dyeing on their own within the framework of oxidative dyeing, but always require the presence of developer components. It is therefore preferred according to the invention that, when at least one coupler component is used, at least one developer component is additionally employed.

Coupler components within the meaning of the invention permit at least one substitution of a chemical residue of the coupler by the oxidized form of the developer component. A covalent bond then forms between coupler and developer component. Couplers are preferably cyclic compounds, which carry at least two groups on the ring, selected from (i) optionally substituted amino groups and/or (ii) hydroxyl groups. If the cyclic compound is a six-membered ring (preferably aromatic), the said groups are preferably located in ortho position or meta position to one another.

Coupler components according to the invention are preferably selected as at least one compound from one of the following classes:
  3-aminophenol (m-aminophenol) and/or derivatives thereof,
  3-aminoaniline (m-diaminobenzene) and/or derivatives thereof,
  2-aminoaniline (1,2-diaminobenzene; o-diaminobenzene) and/or derivatives thereof,
  2-aminophenol (o-aminophenol) and/or derivatives thereof,
  naphthalene derivatives with at least one hydroxy group,
  di- or trihydroxybenzenes and/or derivatives thereof,
  pyridine derivatives,
  pyrimidine derivatives,
  monohydroxyindole derivatives and/or monoaminoindole derivatives,
  monohydroxyindoline derivatives and/or monoaminoindoline derivatives,
  pyrazolone derivatives, such as e.g. 1-phenyl-3-methylpyrazol-5-one, morpholine derivatives, such as e.g. 6-hydroxybenzomorpholine or 6-aminobenzomorpholine,
  quinoxaline derivatives, such as e.g. 6-methyl-1,2,3,4-tetrahydroquinoxaline,
Mixtures of two or more compounds from one or more of these classes are also according to the invention within the framework of this embodiment.

Particularly preferred coupler components according to the invention are selected from among 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxy-pyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts of the aforementioned compounds.

Most particularly preferred here is resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine and 1-naphthol and one of their physiologically acceptable salts.

The coupler components are preferably used in a quantity of 0.005 to 20 wt. %, preferably 0.1 to 5 wt. %, based in each case on the ready-to-use oxidation coloring agent.

Within the framework of the present invention, the following combinations of oxidation dye precursors of the developer type and of the coupler type are particularly preferred. However, still further dye precursors can also be combined with the oxidation dye precursors mentioned as a combination:
p-toluylenediamine/resorcinol;
p-toluylenediamine/2-methylresorcinol;
p-toluylenediamine/5-amino-2-methylphenol;
p-toluylenediamine/3-aminophenol;
p-toluylenediamine/2-(2,4-diaminophenoxy)ethanol;
p-toluylenediamine/1,3-bis(2,4-diaminophenoxy)propane;
p-toluylenediamine/1-methoxy-2-amino-4-(2-hydroxyethylamino)benzene;
p-toluylenediamine/2-amino-3-hydroxypyridine;
p-toluylenediamine/1-naphthol;
2-(2-hydroxyethyl)-p-phenylenediamine/resorcinol;
2-(2-hydroxyethyl)-p-phenylenediamine/2-methylresorcinol;
2-(2-hydroxyethyl)-p-phenylenediamine/5-amino-2-methylphenol;
2-(2-hydroxyethyl)-p-phenylenediamine/3-aminophenol;
2-(2-hydroxyethyl)-p-phenylenediamine/2-(2,4-diaminophenoxy)ethanol;
2-(2-hydroxyethyl)-p-phenylenediamine/1,3-bis(2,4-diaminophenoxy)propane;
2-(2-hydroxyethyl)-p-phenylenediamine 1-methoxy-2-amino-4-(2-hydroxy-ethylamino)benzene;
2-(2-hydroxyethyl)-p-phenylenediamine/2-amino-3-hydroxypyridine;
2-(2-hydroxyethyl)-p-phenylenediamine/1-naphthol;
2-methoxymethyl-p-phenylenediamine/resorcinol;
2-methoxymethyl-p-phenylenediamine/2-methylresorcinol;
2-methoxymethyl-p-phenylenediamine/5-amino-2-methylphenol;
2-methoxymethyl-p-phenylenediamine/3-aminophenol;
2-methoxymethyl-p-phenylenediamine/2-(2,4-diaminophenoxy)ethanol;
2-methoxymethyl-p-phenylenediamine/1,3-bis(2,4-diaminophenoxy)propane;
2-methoxymethyl-p-phenylenediamine 1-methoxy-2-amino-4-(2-hydroxy-ethylamino)benzene;
2-methoxymethyl-p-phenylenediamine/2-amino-3-hydroxypyridine;
2-methoxymethyl-p-phenylenediamine/1-naphthol;
N-(4-amino-3-methylphenyl)-N-[3-(1H-imidazol-1-yl)propyl]amine/resorcinol;
N-(4-amino-3-methylphenyl)-N-[3-(1H-imidazol-1-yl)propyl]amine/2-methylresorcinol;
N-(4-amino-3-methylphenyl)-N-[3-(1H-imidazol-1-yl)propyl]amine/5-amino-2-methylphenol;
N-(4-amino-3-methylphenyl)-N-[3-(1H-imidazol-1-yl)propyl]amine/3-aminophenol;
N-(4-amino-3-methylphenyl)-N-[3-(1H-imidazol-1-yl)propyl]amine/2-(2,4-diaminophenoxy)ethanol;
N-(4-amino-3-methylphenyl)-N-[3-(1H-imidazol-1-yl)propyl]amine/1,3-bis(2,4-diaminophenoxy)propane;
N-(4-amino-3-methylphenyl)-N-[3-(1H-imidazol-1-yl)propyl]amine/1-methoxy-2-amino-4-(2-hydroxyethylamino)benzene;
N-(4-amino-3-methylphenyl)-N-[3-(1H-imidazol-1-yl)propyl]amine/2-amino-3-hydroxypyridine;
N-(4-amino-3-methylphenyl)-N-[3-(1H-imidazol-1-yl)propyl]amine/1-naphthol;
4,5-diamino-1-(2-hydroxyethyl)pyrazole/resorcinol;
4,5-diamino-1-(2-hydroxyethyl)pyrazole/2-methylresorcinol;
4,5-diamino-1-(2-hydroxyethyl)pyrazole/5-amino-2-methylphenol;
4,5-diamino-1-(2-hydroxyethyl)pyrazole/3-aminophenol;
4,5-diamino-1-(2-hydroxyethyl)pyrazole/2-(2,4-diaminophenoxy)ethanol;
4,5-diamino-1-(2-hydroxyethyl)pyrazole/1,3-bis(2,4-diaminophenoxy)propane;
4,5-diamino-1-(2-hydroxyethyl)pyrazole/1-methoxy-2-amino-4-(2-hydroxy-ethylamino)benzene;
4,5-diamino-1-(2-hydroxyethyl)pyrazole/2-amino-3-hydroxypyridine;
4,5-diamino-1-(2-hydroxyethyl)pyrazole/1-naphthol.

In order to achieve a balanced and subtle shade formation, it is advantageous according to the invention if further coloring components are included in the agent that is used in step b) of this variant of the method according to the invention.

In another embodiment, the agents used in step b) of this variant of the method according to the invention can additionally include at least one substantive dye. These are dyes which are absorbed directly onto the hair and do not require an oxidative process to form the color. Substantive dyes are usually nitrophenylenediamines, nitroaminophenols, azo dyes, anthraquinones or indophenols.

The oxidizing agents that the agents which are used in step b) of this variant of the method according to the invention include are similar to those that were described in the blonding variant of the method according to the invention.

The present invention also provides a method for lightening keratin fibers, in particular human hair, wherein
 a pretreatment agent according to the invention is applied onto the fiber, and then
 an agent M2 is used on the fiber, an additional agent M3 being added to the agent M2 before use if desired
 this agent M2 is rinsed off the fiber after a period of 5-60 minutes
 and after the treatment an after-treatment agent M4 is optionally applied onto the fiber and after an exposure time of a few minutes is rinsed off again, at least one of the agents M2, M3 or M4 including at least one oxidizing agent at least one peroxo compound, preferably hydrogen peroxide.

The present invention also provides a method for lightening keratin fibers, in particular human hair, wherein
 a pretreatment agent according to the invention is applied onto the fiber, and then an agent M2 is used on the fiber, which if desired is mixed before use from a lightening agent M2a and an oxidizing agent M2b, this agent M2 is rinsed off the fiber after a period of 5-30 minutes and after the treatment an after-treatment agent M4 is optionally applied onto the fiber and after an exposure time of a few minutes is rinsed off again.

The agents employed in the method according to the invention can therefore be formulated as a one-component agent (agent M2), or as a two-component agent (M2a+M2b) and used accordingly.

A separation into multi-component systems is particularly appropriate where incompatibilities between the ingredients are to be expected or feared; the agent to be employed in the case of these systems is produced by the user directly before use by mixing the component.

A lightening method in which the lightening agent M2a and the oxidizing agent M2b are initially present separately is preferred.

For other preferred embodiments, the statements relating to the agents according to the invention apply mutatis mutandis.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A pretreatment agent for keratinic fibers including, based on its weight,
    a) 0.00001 to 20 wt. % of at least one 4-morpholinomethyl-substituted silicone, which in each case comprises at least one of the structural units of formulae (I), (II) and (III)

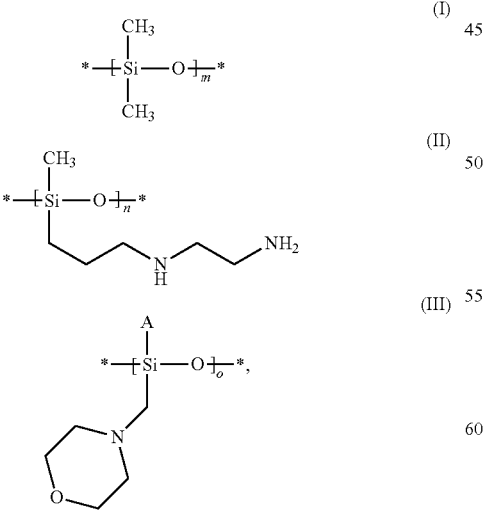

where
  * denotes a bond to one of the structural units (I), (II) or (III) or an end group B (Si-bound) or D (O-bound), B denotes a group —OH, —O—Si(CH$_3$)$_3$, —O—Si (CH$_3$)$_2$OH, —O—Si(CH$_3$)$_2$OCH$_3$, D denotes a group —H; —Si(CH$_3$)$_3$, —Si(CH$_3$)$_2$OH, —Si(CH$_3$)$_2$OCH$_3$, A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, n, m and o denote integers between 1 and 1000, b) at least 50 wt. % water.

2. The agent according to claim 1, wherein the agent includes, based on the weight of the agent, 70 to 99.9 wt. % water.

3. The agent according to claim 1, wherein the agent includes at least one 4-morpholinomethyl-substituted silicone of formula (V)

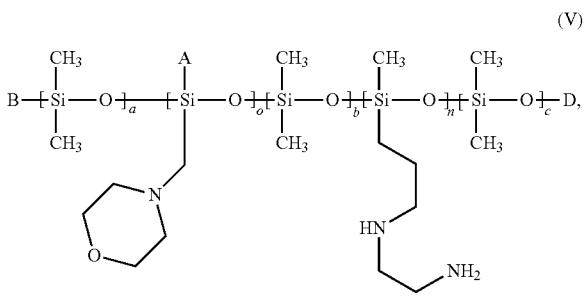

in which

A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, B denotes a group —OH, —O—Si(CH$_3$)$_3$, —O—Si(CH$_3$)$_2$OH, —O—Si(CH$_3$)$_2$OCH$_3$, D denotes a group —H; —Si(CH$_3$)$_3$, —Si(CH$_3$)$_2$OH, —Si(CH$_3$)$_2$OCH$_3$, a, b and c denote integers between 0 and 1000, with the proviso that a+b+c>0 n and o denote integers between 1 and 1000.

4. The agent according to claim 1, wherein the agent includes at least one 4-morpholinomethyl-substituted silicone, which comprises structural units of formula (VI)

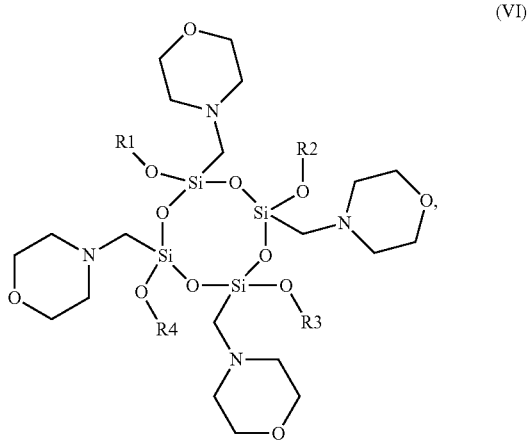

in which
R1, R2, R3 and R4 independently of one another denote —H, —CH$_3$, a group D, a structural unit (I), (II) or (III) or an oligomeric or polymeric residue including structural units of formulae (I), (II) or (III) or
two of the residues R1, R2, R3 and R4 denote a structural unit —Si(R6)(R5)-with
R5=—CH$_3$ or a structural unit of formula (I) or (II) or (III) or an oligomeric or polymeric residue including structural units of formulae (I), (II) or (III)
R6=—OH, —CH$_3$ or a structural unit of formula (I) or (II) or (III) or an oligomeric or polymeric residue including structural units of formulae (I), (II) or (III).

5. The agent according to claim 1, wherein the agent includes at least one 4-morpholinomethyl-substituted silicone, which comprises structural units of formula (VII)

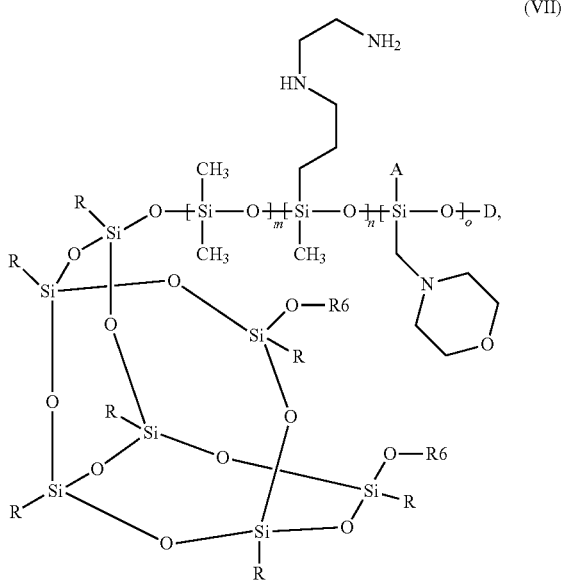

(VII)

in which
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
D denotes a group —H, —Si(CH$_3$)$_3$, —Si(CH$_3$)$_2$OH, —Si(CH$_3$)$_2$OCH$_3$,
R denotes a residue 4-morpholinomethyl,
R6 denotes —H or the grouping

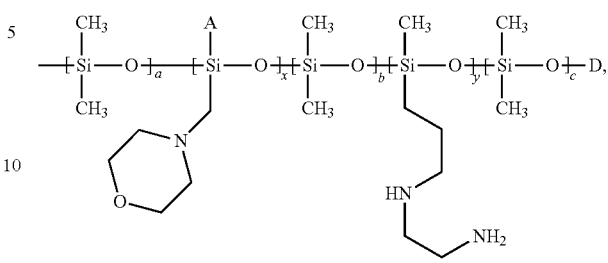

the siloxane units m, n and o respectively a, b, c, x and y being present in random distribution.

6. The agent according to claim 1, wherein the agent includes at least one 4-morpholinomethyl-substituted silicone, in which:
m>(n+o) respectively (a+b+c)>(n+o).

7. A method for oxidative hair treatment, comprising:
a) applying a pretreatment agent according to claim 1 onto the keratinic fibers,
b) subjecting the keratinic fibers to an oxidative hair treatment within a period of one second to 24 hours after step a).

8. The method according to claim 7, wherein step b) encompasses the application of an agent for blonding human hair, which agent includes at least one peroxo compound selected from hydrogen peroxide and its addition compounds on solid carriers, ammonium and alkali metal persulfates and peroxydisulfates.

9. The method according to claim 7, wherein step b) encompasses the application of a hair dye, which includes at least one oxidation dye precursor and at least one oxidizing agent.

10. A method for lightening keratin fibers, in particular human hair, comprising:
applying a pretreatment agent according to claim 1 onto the fibers, and then
applying an agent M2 on the fiber, an additional agent M3 optionally being added to the agent M2 before use if desired,
rinsing the agent M2 off the fiber after a period of 5-60 minutes, and
optionally applying an after-treatment agent M4 onto the fiber and rinsing the agent M4 off after an exposure time of a few minutes,
at least one of the agents M2, M3 or M4 including at least one oxidizing agent at least one peroxo compound.

* * * * *